(12) United States Patent
Hine et al.

(10) Patent No.: US 8,188,252 B2
(45) Date of Patent: May 29, 2012

(54) RAD51 DERIVED CANCER CELL SPECIFIC PROMOTERS FOR TARGETED ANTI-CANCER THERAPY

(75) Inventors: Christopher M. Hine, Rochester, NY (US); Andrei Seluanov, Rochester, NY (US); Vera Gorbunova, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 12/620,103

(22) Filed: Nov. 17, 2009

(65) Prior Publication Data

US 2010/0130596 A1 May 27, 2010

Related U.S. Application Data

(60) Provisional application No. 61/115,232, filed on Nov. 17, 2008.

(51) Int. Cl.
*C07H 21/04* (2006.01)
*C12N 15/63* (2006.01)
*A01K 67/00* (2006.01)

(52) U.S. Cl. ............ 536/24.1; 435/320.1; 435/455

(58) Field of Classification Search .......... None
See application file for complete search history.

(56) References Cited

U.S. PATENT DOCUMENTS

| 7,041,654 B2 * | 5/2006 | Hochberg et al. ........... 514/44 R |
| 2006/0228404 A1 * | 10/2006 | Anderson et al. ............ 424/450 |
| 2009/0123991 A1 | 5/2009 | Rozwadowski et al. |

FOREIGN PATENT DOCUMENTS

WO    WO 01/11369    *    2/2001

OTHER PUBLICATIONS

Maacke et al. DNA repair and recombination factor Rad51 is over-expressed in human pancreatic adenocarcinoma. Oncogene 19:2791-2795, 2000.*
Hine et al. Use of the Rad51 promoter for targeted anti-cancer therapy. PNAS 105:20810-20815, 2008.*
Arias-Lopez et al.; p53 modulates homologous recombination by transcriptional regulation of the RAD51 gene; European Molecular Biology Organization, EMBO Reports, 2006, vol. 7, No. 2; pp. 219-224.
Hasselbach et al.; Characterisation of the promoter region of the human DNA-repair gene Rad51; Eur. J. Gynaec. Oncol.—ISSN: 0392-2936, 2005, XXVI; pp. 589-598.
Heath et al.; Critical Role of STAT5 Activation in Transformation Mediated by ZNF198-FGFR1; The Journal of Biological Chemistry, Feb. 2004, vol. 279, No. 8; pp. 6666-6673.
Russell et al.; Gleevec-Mediated Inhibition of Rad51 Expression and Enhancement of Tumor Cell Radiosensitivity; Cancer Research, Nov. 1, 2003, vol. 63; pp. 7377-7383.

* cited by examiner

*Primary Examiner* — Quang Nguyen
(74) *Attorney, Agent, or Firm* — Hodgson Russ LLP

(57) ABSTRACT

Provided are compositions and methods for inhibiting growth of cancer cells. The method of the invention relates to delivering to cells an effective amount of a composition that contains a polynucleotide having a Rad51 promoter or a polynucleotide having at least 95% similarity to a Rad51 promoter. The Rad51 promoter is operably linked to a coding region for a cytotoxic agent. In vitro and in vivo results demonstrating effectiveness of the polynucleotides of the invention are presented.

4 Claims, 3 Drawing Sheets

SEQUENCE LISTING

<160> NUMBER OF SEQ ID NOS: 15

<210> SEQ ID NO 1
<211> LENGTH: 6532
<212> TYPE: DNA
<213> ORGANISM: human

<400> SEQUENCE: 1

```
gcacagcagg tgagcagcta gcaagcaagc attactgcct gagctctgcc tcctgtcaga     60
tcaaggagag cattagattc tcacaggaac tcaaaaccta ttttgaactg cacctgtgag    120
gaatctagat tgcatactcc ttatggaaat ctaattgatg atcttgaggt gcaacagttt    180
cattccgaaa ccatcctctg cctcatgccc accccccgag ccctgtggaa aattgtcttt    240
cacagaacag ctccctggtg ccaaaaaggt agaactggaa tctaatccaa atcttcatct    300
ctttgttgaa atattgcaag aactcccttt ttggtgtctt cactttcacg ctcctgaaat    360
ctgttcttca acgccacaag gtaatagtgt gaggattaac taaaaacttt gtcaacttta    420
aagcactcca caaatataaa gtagtaataa ggccattgca atggttcaca cctgtaattc    480
caacactttg ggaggccaag gtggaaggat cacttgaggc caggagttca aggccaactt    540
gaacagagcg atatgctgtc tcaaaaataa aaaaataagg ccgggtgcgg tggttcacac    600
ctgtaatccc agcactttgg gaggccacgg taggtggatc acctgaggtc aggagttcga    660
gaccagcctg gccaacatgg tgaaaccctg tctctactaa aaatacaaaa aattagctgg    720
gcgtggtggc aggcgcctgt aatcccagtt acttgggagg ctgaggcagg aagactcgct    780
tgaatctggg aggtggggtt gcagtgagct gataccacgt ccctgcactc cagcctgggc    840
aacagagcaa gactccatct aaaatagata aataaataaa taataaaaa taaaacccct    900
ttgggaagtg gagggaaaat agatctaacc aaatgacttg tcttcttaaa aacttcaatg    960
atttcttcag tacctagaga ccaaagctcc ttaccttttt ttttttttt gagacggagt   1020
cttgctctgt tgcccaggct ggagtgcagt ggcgtgatct cgctcactgc aacctccacc   1080
tcccgggttc aagcacttct ctgcctcagc ctcccaaaga gctgggatta caggcatgca   1140
ccaccacgcc cggctaattt ttgtagtttt agtagagatg gggttttgcc atcttggcca   1200
ggctggtctt gaactcctga cctcgtgatc cgcccacctt ggcctcccaa agttctggga   1260
ttacaggctt gagccaccgc gcctggcctc tccttacatg ttttgttgtt gtcgcttgtc   1320
ttttgagaca aggtctcact ctgtagccca ggctggagtg cagtggccca tcatagctca   1380
ctgcagcctt gacgtcctga gctcaagcag tcctcccacc tcagcctccg ggatagctga   1440
gaccacaggc acaagccacc acgcccagct tattttattt tattttttt tgagatatgg   1500
ggtcccacta tgttgcccag gctggtctcc aactcctgag ctcaagcgat cctcccccac   1560
cttggcttcc caaagtgctg ggattacagg tgtgagccac cgtgcaggcc ttatatgatc   1620
ttcatatcct gaactaaatg taaccttcca gtttcggcac ttgctctggc acttttcctc   1680
cctcgccaga taatactaat cttiaatcat gtagttcgtt ccatgccca tactaccta    1740
tttgcttata atgtcttcca cttcgcccaa gaatccctac tcagctagct tgtggtgttg   1800
ttttgacaca gtctcgctct gtcgcccagg ctggagtaca gcggcgagat ctcggttggc   1860
tgcaacctcc tcctgagttc aagcgattct cgtgcctcag cctttcgagt agctaggatt   1920
acaggcatgt gccacaaaac ctggctaatt tttgtatttt ttactaaaga cgaggtttca   1980
ccacgttggc caggtttatc tccaaccccg gacctcaggt gatccgcctg ccttggcctc   2040
```

```
ctaaactgct gggattactg gcgtgaacca ccgcgcccgg ccctactcag cctttaaaac   2100
cggaatcacg ggtcaaaact ttctggtaaa ccacgatacg gtttaggtta tgaaattcaa   2160
tgccccsttc ctctgaactc ctgcaaatct ccagtaaagc accacagatt gacgaatatt   2220
ccagccattt ccctctcccg tacgctagct ccatttccca cttctatcca tcttctcgag   2280
cttcctcagc tcctccacct ccatgaggcc tggaaagcac cttgctccag gaatgcgagt   2340
aggaggctca gagcgaccag aagtgccaaa agctgacatt cagatactgc cgaaacaaac   2400
cacaagagcg ctagggcccc cgctaatagt ccagctgcga tggtgagaac tcgcggaccc   2460
gccggcgatg catgccggga gatgtagtcc cgggccgacg cattacctct tgggagtcgt   2520
ggtcttcgat ctggtaaaca aagacggca actcggttaa gtcttccccc accgccccct   2580
gaaatccctc gccccacccg cgagggactg ggtaggagt aggggcgttg ccgtggttag   2640
cctcgaactc ctaggctcag acgatactct cgcctcggcc tcccgagcag ctgggactac   2700
acgcgtgagc caccgccccc ggcataaagt ttgaattagt ccttacgcaa aaagggaaga   2760
gggcagtctg taaactcgcg caggatcaag ctctcgagct cccgtcttgg gttagcgcgc   2820
agggcggaag cggggagaag gcggatccgg gaggcgggga tacgttacgt cgacgcgggc   2880
gtgaccctgg gcgagagggt ttggcgggaa ttctgaaagc cgctggcgga ccgcgcgcag   2940
cggccagaga ccgagccta aggagagtgc ggcgcttccc gaggcgtgca gctgggaact   3000
gcaactcatc tgggttgtgc gcagaaggct ggggcaagcg agtagagaag tggagcgtaa   3060
gccaggggcg ttgggggccg tgcgggtcgg gcgcgtgcca ctcccgcggg gtgaagtcgg   3120
agcgcggggc ctgctggaga gaggagcgct gcggaccgag gtgagtgtgt gaggcgcagg   3180
ctgggccctc cagagccgcg gctcgtcctc gcccacctgc gtcctggccg gtccagtgct   3240
cagcggcagt tggggcctcc gcgcgcagtg tgaaacccgg acgtggcagg gcgtgtccgc   3300
gcccgaccga ccctcagctg ctggggcgaa aacacaagtg gacctcagtc tttagaacta   3360
ggggagaaac attagagcct ttataggcaa cacctatttt atgggttcga gcgagaagtc   3420
cgagatcaga gcggtgtagc cacagctgtt aatatcaca gccagggctt ccggattcct   3480
gatctgtcct tccattacac cgtgcttaga aagtaccaat ctccgattgc caaaacagtg   3540
ttttcatcat ctaatgcgga aaaccattca catgatgcct agagaatgat ctgaagtgag   3600
gttttggtttt cttaaaactt tttttttgag atggagtctc gctcttccgc ccaggctgga   3660
gtgtagtggc gcgatctcgg ctcactgcaa cctccgcctc ccggattcaa gcgattctcc   3720
tacctcagcc tcccgaggag ctgggattac aggcccccac caccacgccg ccaggctgat   3780
ttttgtattt ttagtagaga cggggtttca ccatgttggt caggctggtc tcgaacttct   3840
gacctcaggt tatccacccg cctctgcctc ccaaagtgct gggattacag ccgtgagcca   3900
cagcgcctgg gcctgttttt tttgtttgtt tgtttgtttt taacttctaa agcgcaatgt   3960
aatatacatg tagaaaaatt cacattcaca actgtataca actccgtgaa ttattacaaa   4020
atatactggc cgggcgtcgt gtctcacgtc tgtagtccca gcactttggg aagtggaggc   4080
gggaggacga ttgagcccaa gagttcgaga acagcctggt caagatagtg agacccgcat   4140
ctctacaaat aggaaaaatt agctaggcat ggtggcgtgc acctgtaggc ccagctattc   4200
aggaggctga gaaggagga tctagcctgg gaggtataag ctgcagtgag ctgtgatcag   4260
gccactgcac tccaacctgg gcgatagagc aagacaaaat gaatatacac ctatgtaatc   4320
accacttaat agaatggtcc tcagaagcct tcctgtgtag tatttaatat tttccccttt   4380
ttacagtggt aactgctata ctggttttcta atgagatgaa ctaatgttgc ttgttttga   4440
```

```
attttatata aaaatacatc aggagtgttg agtgtttcgt tgtttcacat gcttgccaac    4500
acgatatttt tcagccttt tgattttaac tattctgctg gttacacagt aatgtctcaa    4560
tgtgatttta attttcctga ttaataatga tgttggacat ctgttcatat gttttgccc    4620 attttgatat cttctgtgat gtgcttgttc aaatctcttg cctattttc tattatcttt    4680 ttcttactga tgtgaagttc tttatatact ggttatcagc cctcagttat gtttgtgcta    4740
aatgttttct ctactgtggt ttgacttgtc actctcttag tggtgtcctt tgatgaatag    4800
aagtgctgaa tttattttt tattatttat ttatttattt attttccctt ttgagacaga    4860
gtttggctct tgttgcccag gctggagtgc aatggcacaa tcttggctca ccgcaacctc    4920
cgcctcctgg gttcaagcga ttctcctgcc tcagcctccc gagtagctgg gattacaggc    4980
atgtgccacc acgcccagct aattttgtat ttttctttaa tagagacagg atttctccat    5040
gttggtcagg ctggtcttga actcctgaac ttaggtgatc tgcccgcctt ggcctcccaa    5100
agtgctggga ttgcagacgt gagccacagt gcccagtaga agtgctgaat ttaaatgtag    5160 ttcagtttc agtcttttcc tttttggcta gtgcgttatg catccagttt caagaaatct    5220
ttttctgtcc caaggttgtg aaaataataa gtgttacttt gttttgaca gacgattgta    5280 catatttatg agatacaaga tgatatttct tttttttttt tttttttttt gagacggagt    5340
ctcactctgt cgcccaggct ggagtgcagt ggcgcgatct tggctcactg caagctccgc    5400
ctcctgggtt cacgccattc tcctgcctca gcctgccacc acgcccagct aattttttgt    5460 atttttagt agagacaggg tttcaccatg ttagccagga tggtctcgat ctcctgacct    5520
cgtgatccac cgccttggc ctcccaaagt gctgggatta caggcgtgag ccactccacc    5580
tggcccaaga tgatatttca atacatatat acattgtata atgaatgatc aaatcagggt    5640
aatcagcata tccatcagtt cacttaaaca cttgtcattt ctctttgtga tgagaacatt    5700
caaaatactc gcttctggct attttgaagt atacattaca ttagtgttta ctgtagtcac    5760
cctactgtga aatagaaccc tagaacttat tcctcctatc taactgaaac tttgtgcctg    5820
ttgaccaacc tctctccttc ctgccgcccc ctgcaacagc tgcattctcc tcagtctctg    5880
gttaccactc ttctatttgt tccttgtatg agatgaactt ttttttttt gtttttttt    5940 ttgagacaca gtctcactct gtcatgaggc tggagtacag tggcacgatc tcggctcact    6000
gcgatctctg tcttccgggt tgaagccatt tacctgcctc agcctcccga gtagctggga    6060
ctacaggcgt gtgccaccac accctgctaa tatttgtatt tttagtaggg acggggtttc    6120
gcatgttggc cggatggtc ttgatctcct gacctggtga tctgcccgcc tcggcctccc    6180
aaagtgctgg gatcacaggc atgagccacc gcgcccgcc aagatcaact ttttagatt    6240 ctacatatga gtgagatcat gcagtatttg tctgcaaaca catttataat gtataatggg    6300
gtatataaaa ataagtaaaa cttggcccct acactgaagg aatataaagc aggagaacag    6360
agaggcacaa taagagaatg gccttggctt ttcctaaagt cttttgata cgactagcta    6420 gatagaagat ggggagagag atgcaccta ttttctctagt gttatactg ataagcatt    6480 gtatttttca gtaatggcaa tgcagatgca gcttgaagca aatgcagata ca    6532
```

<210> SEQ ID NO 2
<211> LENGTH: 46
<212> TYPE: DNA
<213> ORGANISM: human

<400> SEQUENCE: 2

```
tgtaaactcg cgcaggatca agctctcgag ctcccgtctt gggtta                  46
```

<210> SEQ ID NO 3
<211> LENGTH: 11
<212> TYPE: DNA
<213> ORGANISM: human

<400> SEQUENCE: 3

```
tttggcggga a                                                            11
```

<210> SEQ ID NO 4
<211> LENGTH: 654
<212> TYPE: DNA
<213> ORGANISM: Corynebacterium Diphtheriae

<400> SEQUENCE: 4

```
atggatcctg atgatgttgt tattcttcta atcttttgta tggaaaactt ttcttcgtac     60
cacgggacta aacctggtta tgtagattcc attcaaaaag gtatacaaaa gccaaaatct    120
ggtacacaag gaaattatga cgatgattgg aaagggtttt atagtaccga caataaatac    180
gacgctgcgg gatactctgt agataatgaa aacccgctct ctggaaaagc tggaggcgtg    240
gtcaaagtga cgtatccagg actgacgaag gttctcgcac taaaagtgga taatgccgaa    300
actattaaga aagagttagg tttaagtctc actgaaccgt tgatggagca agtcggaacg    360
gaagagttta tcaaaaggtt cggtgatggt gcttcgcgtg tagtgctcag ccttcccttc    420
gctgagggga gttctagcgt tgaatatatt aataactggg aacaggcgaa agcgttaagc    480
gtagaacttg agattaattt tgaaacccgt ggaaaacgtg gccaagatgc gatgtatgag    540
tatatggctc aagcctgtgc aggaaatcgt gtcaggcgat ctctttgtga aggaacctta    600
cttctgtggt gtgacataat tggacaaact acctacagag atttaaagct ctaa          654
```

<210> SEQ ID NO 5
<211> LENGTH: 217
<212> TYPE: PRT
<213> ORGANISM: Corynebacterium Diphtheriae

<400> SEQUENCE: 5

```
Met Asp Pro Asp Asp Val Val Ile Leu Leu Ile Phe Cys Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175
```

```
Ala Met Tyr Glu Tyr Met Ala Gln Ala Cys Ala Gly Asn Arg Val Arg
            180                 185                 190

Arg Ser Leu Cys Glu Gly Thr Leu Leu Leu Trp Cys Asp Ile Ile Gly
        195                 200                 205

Gln Thr Thr Tyr Arg Asp Leu Lys Leu
        210                 215

<210> SEQ ID NO 6
<211> LENGTH: 39
<212> TYPE: DNA
<213> ORGANISM: Artificial Sequence
<220> FEATURE:
<223> OTHER INFORMATION: Rad51 PCR promoter for first step of cloning

<400> SEQUENCE: 6
aacattaatg cacagcaggt gagcagctag caagcaagc                              39

<210> SEQ ID NO 7
<211> LENGTH: 44
<212> TYPE: DNA
<213> ORGANISM: Artificial Sequence
<220> FEATURE:
<223> OTHER INFORMATION: Rad51 promoter PCR primer 2 for first step
      cloning

<400> SEQUENCE: 7
cgcaccggtg ccattactcg gtccgcagcg ctcctctctc cagc                        44

<210> SEQ ID NO 8
<211> LENGTH: 30
<212> TYPE: DNA
<213> ORGANISM: Artificial Sequence
<220> FEATURE:
<223> OTHER INFORMATION: Rad51 promoter-3 for second step cloning

<400> SEQUENCE: 8
tctgtaaact cgcgcaggat caagctctcg                                        30

<210> SEQ ID NO 9
<211> LENGTH: 39
<212> TYPE: DNA
<213> ORGANISM: Artificial Sequence
<220> FEATURE:
<223> OTHER INFORMATION: Rad51 promoter PCR primer-4 for second step
      cloning

<400> SEQUENCE: 9
tccaccggtg tatctgcatt tgcttcaagc tgcatctgc                              39

<210> SEQ ID NO 10
<211> LENGTH: 35
<212> TYPE: DNA
<213> ORGANISM: Artificial Sequence
<220> FEATURE:
<223> OTHER INFORMATION: Rad51-luciferase primer 1 for cloning

<400> SEQUENCE: 10
ccggaagctt accggtcgcc accatggaag acgcc                                  35

<210> SEQ ID NO 11
<211> LENGTH: 32
<212> TYPE: DNA
<213> ORGANISM: Artificial Sequence
<220> FEATURE:
<223> OTHER INFORMATION: Rad51 luciferase PCR primer-2 for cloning
```

```
<400> SEQUENCE: 11
gccaagctta attaattcgc agatctcgag cc                                    32

<210> SEQ ID NO 12
<211> LENGTH: 37
<212> TYPE: DNA
<213> ORGANISM: Artificial Sequence
<220> FEATURE:
<223> OTHER INFORMATION: Rad51-DTA primer-1 for cloning

<400> SEQUENCE: 12
ttagcggccg cttagagctt taaatctctg taggtag                               37

<210> SEQ ID NO 13
<211> LENGTH: 35
<212> TYPE: DNA
<213> ORGANISM: Artificial Sequence
<220> FEATURE:
<223> OTHER INFORMATION: Rad51 promoter PCR primer-2 for cloning

<400> SEQUENCE: 13
cctaccggtc gccaccatgg atcctgatga tgttg                                 35

<210> SEQ ID NO 14
<211> LENGTH: 28
<212> TYPE: DNA
<213> ORGANISM: Artificial Sequence
<220> FEATURE:
<223> OTHER INFORMATION: Rad51 promoter-1 for RT-PCR

<400> SEQUENCE: 14
ccagagaccg agccctaagg agagtgcg                                         28

<210> SEQ ID NO 15
<211> LENGTH: 30
<212> TYPE: DNA
<213> ORGANISM: Artificial Sequence
<220> FEATURE:
<223> OTHER INFORMATION: Rad51 PDR primer-2 for Rad51 RT-PCR

<400> SEQUENCE: 15
tggcatttat gccacactgc tctaaccgtg                                       30
```

RAD51 DERIVED CANCER CELL SPECIFIC PROMOTERS FOR TARGETED ANTI-CANCER THERAPY

This application claims priority to U.S. Provisional Patent Application No. 61/115,232, filed on Nov. 17, 2008, the disclosure of which is hereby incorporated by reference in its entirety.

This invention was made with government support Grant Number GM068411 from the National Institutes of Health. The government has certain rights in the invention.

FIELD OF THE INVENTION

The present invention relates generally to cancer therapy and more specifically to compositions and methods for targeting cancer cells with a cytotoxic agent, the expression of which is driven by a Rad51 promoter.

BACKGROUND OF THE INVENTION

The goal of cancer treatment is to selectively inhibit or eliminate the growth of malignant cells while leaving normal tissue intact. Transcriptionally targeted anti-cancer therapy employs an elegant approach to selectively destroy cancer cells by placing a cytotoxic gene/oncolytic virus under transcriptional control of cancer specific promoters. To date several attempts to design such systems have been made. For example, the telomerase RNA subunit hTER and catalytic subunit hTERT (Abdul-Ghani R, et al. (2000) Mol Ther 2: 539-44; Koga S, et al. (2000 Hum Gene Ther 11: 1397-406; Komata T, et al. (2001) Cancer Res 61: 5796-802; Kirch H C, et al. (2002) Oncogene 21: 7991-8000; Majumdar A S, et al. (2001) Gene Ther 8: 568-78; Gu J, et al. (2000) Cancer Res 60: 5359-64, tyrosinase (Nettelbeck D M, et al. (2002) Cancer Res 62: 4663-70), prostate antigen (Latham et al. (2000) Cancer Res 60: 334-41), survivin (Chen J S, et al. (2004) Cancer Gene Ther 11: 740-7), and midkine genes (Yu L, et al. (2004) Eur J Cancer 40: 1787-94) have been proposed for use in transcriptional targeting of cancers. However, limitations of these promoters include insufficient expression of therapeutic genes, leaky expression resulting in toxicity to normal cells, and narrow specificity to a particular tumor type. Thus, there is an ongoing need to provide improved compositions and methods suitable for use in transcriptional targeting of cancer cells. The present invention meets this need.

SUMMARY OF THE INVENTION

The present invention provides compositions and methods for inhibiting growth of cancer cells. The invention is surprisingly superior to previously available methods for inhibiting the growth of cancer based on various promoter/cytotoxic agent configurations.

The method comprises delivering to the cells an effective amount of a composition comprising a polynucleotide which contains a Rad51 promoter operably linked to a coding region for a cytotoxic agent.

In one embodiment, the Rad51 promoter used in the invention comprises the sequence of SEQ ID NO:1, or a sequence having at least 95% homology to SEQ ID NO:1. In another embodiment, the promoter comprises a fragment of SEQ ID NO:1, or a polynucleotide that is at least 95% homologous to the fragment of SEQ ID NO:1.

In one embodiment, the Rad51 promoter that is a fragment of SEQ ID NO:1 is from and including nucleotide position 2,701 through and including nucleotide 6,493 of SEQ ID NO:1, or a sequence having at least 95% homology to the sequence from and including nucleotide position 2,701 through and including nucleotide 6,493 of SEQ ID NO:1.

The compositions of the invention contain polynucleotides comprising a Rad51 promoter operably linked to a coding region for a cytotoxic agent or for a reporter gene, and having the Rad51 sequences as described above for use in the method of the invention.

The methods and compositions of the invention are demonstrated to selectively inhibit growth of cancer cells via transcriptional targeting both in vitro and in an animal model of cancer. The invention is expected to be effective against any cancer cells, but is particularly suited for use in treating solid tumors. In particular, the invention is demonstrated to kill a variety of cancer cells in vitro, and to reduce the mass of established tumors and inhibit tumor angiogenesis in an animal model.

DETAILED DESCRIPTION OF THE INVENTION

Figure 1:
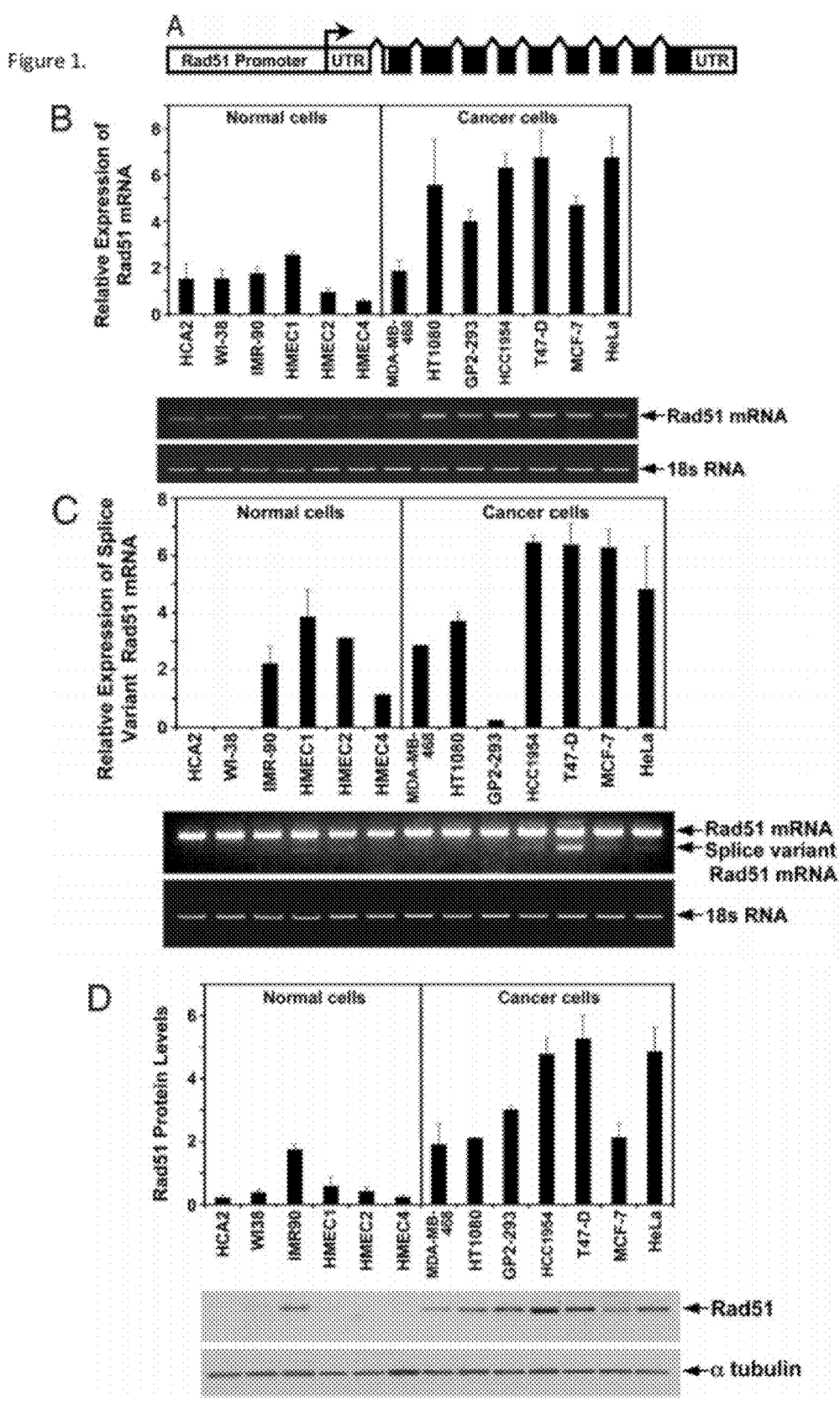
FIGS. 1A-1D illustrate that Rad51 mRNA and protein levels are increased in cancer cells. (A) Diagram of the human Rad51 gene. Transcription start site is indicated by arrow. Coding exons are represented by solid black boxes. Upstream to the start of transcription is the Rad51 regulatory region. (B) Analysis of Rad51 transcript levels in normal and cancerous cells by quantitative RT-PCR. The top bands are RT-PCR products of Rad51 mRNA and the bottom bands are RT-PCR products of 18S subunit ribosomal RNA used as a reference. The histogram represents the relative intensity of the Rad51 band normalized to the 18S band. (C) Analysis of alternatively spliced Rad51 transcript levels by quantitative RT-PCR. Same PCR primers are used as in B but the number of the PCR cycles is increased and the gel is overexposed to visualize the less abundant alternative splice variant of Rad51. The top band is full length (not quantified because of saturation), and the band directly below it is the alternative slice variant. The histogram represents the relative intensity of the Rad51 splice variant band with the 18S band used as a reference. (D) Western blot analysis of Rad51 protein. Protein levels for each cell line were normalized using α-tubulin as a loading control and are displayed in the histogram above the gels. All the experiments were repeated three times and error bars are s.d.

The present invention involves transcriptional targeting of cancer cells. The invention provides compositions and methods for inhibiting growth of cancer cells that entail exploiting newly discovered transcriptional differences in cancer cells relative to normal cells, such transcription under control of a Rad51 promoter.

The method comprises delivering to cancer cells an effective amount of a composition comprising a polynucleotide, wherein the polynucleotide comprises a Rad51 promoter, wherein the Rad51 promoter is operably linked to a coding region for a cytotoxic agent, and wherein subsequent to delivering the composition to the cancer cells the growth of cancer cells is inhibited. The invention is based on the unexpected discovery that by replacing all or most of the Rad51 protein coding sequence with an alternative protein coding sequence, such as a sequence encoding a reporter gene or a cytotoxic agent, the Rad51 promoter activity in cancer cells relative to non-cancer cells is dramatically increased as described in greater detail below.

By "operably linked" it is meant that the Rad51 promoter effects transcription of a coding region via recruitment of transcription factors that bind to the Rad51 promoter and participate in transcription of a polynucleotide sequence that comprises the coding region for a cytotoxic agent or a reporter protein. The Rad51 promoter sequence used herein may or may not be contiguous with the coding region to which it is operably linked. For example, the 3' most nucleotide of the Rad51 promoter sequence may be upstream and immediately adjacent to the first transcribed nucleotide of the coding region, or there may be intervening nucleotide sequences, which can include but are not limited to nucleotides that are involved in splicing, or nucleotides that are part of an mRNA encoding the cytotoxic agent but are not themselves part of a translated exon.

Compositions provided by the invention include polynucleotides comprising a Rad51 promoter operably linked to a coding region for a cytotoxic agent. The composition can comprise any polynucleotide comprising a Rad51 promoter operably linked to a coding region for a cytotoxic agent as described herein in connection with the method of the invention. A composition of the invention also includes the Rad51 promoters as described herein operably linked to a coding region for a reporter gene, examples of which include but are not limited to luciferase and green fluorescent protein (GFP).

The methods and compositions of the invention are demonstrated to selectively inhibit growth of cancer cells both in vitro and in an animal model of cancer as described further below. It is expected that the invention can be used to inhibit the growth of any type of cancer cells. In non-limiting embodiments, the invention facilitates inhibiting growth of breast cancer cells, cervical cancer cells, fibrosarcoma cells, kidney cancer cells, prostate cancer cells, on-small-cell lung cancer, or any combination thereof.

In one embodiment, the method of the invention is used to inhibit cancer cell growth as evidenced by decreased mass in a solid tumor, relative to a tumor to which a composition of the invention is not delivered. In another embodiment, the invention causes reduced angiogenesis in a tumor, relative to a tumor to which a composition of the invention has not been administered.

In one embodiment, the method comprises administering to an individual an effective amount of a composition comprising a polynucleotide, wherein the polynucleotide comprises a Rad51 promoter, wherein the Rad51 promoter is operably linked to a coding region for a cytotoxic agent, and wherein subsequent administering the composition to the individual the growth of cancer cells in the individual is inhibited.

The sequence of the human Rad51 gene, including the promoter, is known in the art and can be accessed via GenBank accession no. NG_012120. In one embodiment, the Rad51 promoter used in the invention comprises the sequence of SEQ ID NO:1. In an alternative embodiment, the Rad51 promoter comprises a sequence having at least 95% homology to SEQ ID NO:1. The terms "homology" and "homologous" as used herein in reference to polynucleotides mean similarity between polynucleotide sequences. The Rad51 promoter used in the invention may have at least 95%, 96%, 97%, 98% or 99% homology to SEQ ID NO:1. In further embodiments, the Rad51 promoter used in the invention comprises a fragment of SEQ ID NO:1, or a polynucleotide having at least 95% homology to a fragment of SEQ ID NO:1. Rad51 promoters that have at least 95% homology to SEQ ID NO:1 or a fragment thereof further comprise sequence and functional attributes that are further described below.

Rad51 promoters and fragments thereof suitable for use in the invention that are not identical to SEQ ID NO:1, but are at least 95% homologous to it or a fragment thereof, may differ from SEQ ID NO:1, by for example, nucleotide additions, deletions or substitutions. However, such promoters share not only the specified amount of structural similarity (e.g., at least 95% homology) to SEQ ID NO:1 or a fragment thereof, but are also characterized by the capability to preferentially drive expression in cancer cells of a protein encoded by the sequence to which the promoter is operably linked. In this regard, while it is known that Rad51 protein is ordinarily overexpressed by an average of 5-fold in cancer cells which is generally regarded as inadequate for transcriptional targeting, as mentioned above, disclosed herein for the first time is the unexpected discovery that by replacing all or most of the Rad51 protein coding sequence with an alternative protein coding sequence, such as a sequence encoding a reporter gene or a cytotoxic agent, the Rad51 promoter activity in cancer cells relative to non-cancer cells is dramatically and unexpectedly increased. For example, using a Rad51 promoter to drive expression of luciferase, we demonstrate from 800 fold to 12,500 fold greater luciferase activity in cancer cells relative to non-cancer cells, which is indicative of a correlative increase in transcription (and translation) of the luciferase gene to which the Rad51 promoter is operatively linked. Thus, in one embodiment, a Rad51 promoter used in the invention that is not identical to SEQ ID NO:1 but is at least 95% homologous to SEQ ID NO:1 or a fragment thereof is capable of driving expression of luciferase in cancer cells and non-cancer cells, such that luciferase activity in the cancer cells is from 800 fold to 12,500-fold greater than in non-cancer cells comprising the same Rad51 promoter sequence operably linked to the same luciferase coding sequence. Those skilled in the art, given the benefit of the present invention, can readily envision and if desired test sequences that are at least 95% homologous to SEQ ID NO:1 or a fragment thereof which have such functional and structural attributes.

We also demonstrate that by transfecting cancer cells with a polynucleotide encoding a representative cytotoxic agent (bacterial diphtheria toxin A), the expression of which is driven by a Rad51 promoter as described herein, we can achieve inhibition of protein synthesis of up to 100,000 fold relative to protein synthesis in non-cancerous cells. Further, the invention to preferentially inhibit growth of cancer cells not only in vitro, but also in an animal model by reduction in tumor mass. Further still, the compositions and methods of the invention are shown to inhibit angiogenesis in tumors in animal models relative to control animals. The present invention therefore provides surprisingly superior compositions and methods for selectively killing and/or inhibiting the growth of cancer cells relative to previously available transcriptional targeting schemes.

In one embodiment, the Rad51 promoter consists of SEQ ID NO:1, and thus does not contain any other portion of the Rad51 gene. In another embodiment, the promoter is a fragment of SEQ ID NO:1 that has at its 5' end the nucleotide at position 2,701 of SEQ ID NO:1, and at its 3' end the nucleotide at position 6,493 of SEQ ID NO:1. This construct also exhibited low activity in non-cancer cells (normal human skin fibroblasts), but expression in human cervical carcinoma cells (HeLa) increased approximately 2 fold over what was observed with the longer Rad51 promoter region (SEQ ID NO:1). Specifically, testing of the shortened Rad51 promoter versus the full length of SEQ ID NO:1 was by firefly luciferase analysis using normal human skin fibroblasts and the HeLa cells. There was no significant difference in relative light units (RLU) between the full length and shortened promoter in normal fibroblasts, but in the HeLa cells the shortened promoter produced two fold more RLU than the full length promoter.

In one embodiment, the Rad51 promoter consists of a fragment of SEQ ID NO:1 that has at its 5' end the nucleotide at position 2,701 of SEQ ID NO:1, and at its 3' end the nucleotide at position 6,493 of SEQ ID NO:1, and does not contain any other portion of the Rad51 gene. In one embodiment, the fragment of SEQ ID NO:1 is a fragment of SEQ ID NO:1 that is at least 3,793 nucleotides in length, or is a fragment of a polynucleotide that is least 3,793 nucleotides in length and has at least 95% homology to a fragment of SEQ ID NO:1 that is also at least 3,793 nucleotides in length.

In alternative embodiments, the polynucleotide may be at least 3,793 nucleotides in length, and up to 6,523 nucleotides in length, including all integers there between. It will be recognized that reference to nucleotide length herein refers to the sequence of one strand of a double stranded promoter, and therefore reference to nucleotide length and SEQ ID NO:s contemplate double stranded promoters where the referenced sequence is annealed to its reverse complement.

In another embodiment, the Rad51 promoter comprises a sequence having at least 95% homology to the fragment of SEQ ID NO:1 that has at its 5' end nucleotide 2,701 and at its 3' end nucleotide 6,493 of SEQ ID NO:1. Thus, the Rad51 promoter may consist of a sequence that has at least 95% homology to the sequence bounded by and including the nucleotide at nucleotide position 2,701 and ending at nucleotide position 6,493 of SEQ ID NO:1.

The Rad51 promoter used in the invention preferably comprises certain regulatory elements. In one embodiment, the Rad51 promoter includes the sequence tgtaaactcgcgcaggatcaagctctcgagctcccgtcttgggtta (SEQ ID NO:2), which is believed to function as a p53 binding domain. (See, for example, Arias-Lopez et al., EMBO (2006), Vol. 7, pp 219-224). In another embodiment, the Rad51 promoter comprises the sequence tttggcgggaa (SEQ ID NO:3), which is considered to be an overlapping binding site for E2F4/Stat5. (See, for example, Hasselbach L, et al. (2005) Eur J Gynaecol Oncol 26: 589-98). It is preferable for the Rad51 promoter to comprise both SEQ ID NO:2 and SEQ ID NO:3, and that these sequences are not altered, should the Rad51 promoter comprise a sequence that is not identical to SEQ ID NO:1 or a fragment thereof. Thus, in one embodiment, the invention uses a Rad51 promoter that is at least 95% homologous to SEQ ID NO:1, and wherein the promoter comprises the sequences of SEQ ID NO:2 and SEQ ID NO:3, and wherein SEQ ID NO:2 and SEQ ID NO:3 are within the context of SEQ ID NO:1.

In one embodiment, the last nucleotide of SEQ ID NO:2 is the $177^{th}$ nucleotide upstream from the first transcribed nucleotide of the mRNA encoding the cytotoxic agent. In another embodiment, the last nucleotide of SEQ ID NO:3 is the $21^{st}$ nucleotide. The first transcribed nucleotide is illustrated for reference in SEQ ID NO:1 by the nucleotide at position 2,930. Since the Rad51 promoter lacks a TATA box (also called Goldberg-Hogness box), the actual first nucleotide incorporated into the RNA can vary, but such variation is not believed the affect performance of the invention.

Nucleotide 6,494-6,532 of SEQ ID NO:1 (nucleotide 6,532 being the most 3' nucleotide of the sequence shown in SEQ ID NO:1) encode an N-terminal amino acid sequence of Rad51. The AUG initiating codon begins at position 6,494. This Rad51 coding sequence may be present in the compositions used in the method of the invention and if so, may be provided such that the AUG codon beginning at position 6,494 is in-frame with the sequence encoding the cytotoxic agent to which the Rad51 promoter is operably linked. Thus, in one embodiment, the cytotoxic agent may be translated as a fusion protein which comprises at its N terminus a portion of the Rad51 amino acid sequence. This configuration of an N-terminal portion of the Rad51 protein fused to the N-terminus does not affect the activity of diphtheria toxin and is expected not to affect the activity of other cytoxic agents, if such fusion proteins are encoded by a composition of the invention. The two nucleotides upstream of the AUG codon beginning at position 6,494 of SEQ ID NO:1 are believed to be required for proper splicing of the mRNA.

It is expected that any cytotoxic agent that can be transcribed, and/or transcribed and translated can be used in the invention. Non-limiting examples of polypeptide cytotoxic agents suitable for use in the invention include but are not limited to *Pseudomonas* exotoxin, *Pseudomonas* endotoxin, ricin A, saporin, abrin, ribonuclease, DNase I, Staphylococcal enterotoxin-A, pokeweed antiviral protein, gelonin, diphtheria toxin a (DTA), tumor necrosis factor alpha, *Crotalus*

*durissusterrificus* toxin, *Crotalus adamenteus* toxin, *Naja naja* toxin, *Naja mocambique* toxin, cytotoxic inhibitory RNAs and cytotoxic inhibitory dominant negative peptides. DNA sequences encoding the aforementioned cytotoxic agents and the amino acid sequences of the cytotoxic agents are known in the art.

In one embodiment, the cytotoxic agent is bacterial diphtheria toxin A. A DNA sequence encoding bacterial diphtheria toxin A is provided as SEQ ID NO:4. The amino acid sequence of bacterial diphtheria toxin A is provided as SEQ ID NO:5.

The polynucleotide comprising the Rad51 promoter operably linked to a coding region for a cytotoxic agent may be provided within the context of any suitable expression vector. Suitable expression vectors into which the polynucleotides of the invention can be inserted are commercially available. In general, they can contain appropriate eukaryotic translation signals, and may contain additional elements, such as polyadenylation and/or protein trafficking signals. In one embodiment, the expression vector comprises a bacterial origin of replication, but not a mammalian origin of replication. In alternative embodiments, pseudotyped lentiviral vectors targeted to prostate cells containing a prostate specific promoter to control gene of interest expression can be used to deliver the polynucleoides of the invention (Pariente N, et al. (2007) Mol Ther 15: 1973-81). Additionally, the Rad51 promoter can be used to specifically express a cytoxic gene and/or a reporter gene in a replication deficient virus by the substitution of the adenoviral E1A genes with Rad51 promoters described herein. Alternatively, the Rad51 promoters can be used to control the expression of the E1A genes in what is known as a conditionally replicating adenovirus, thus providing another embodiment that would permit the virus to selectively kill cancer cells.

The expression vectors or other polynucleotide comprising the Rad51 promoter operably linked to a cytotoxic agent may be formulated in any pharmaceutically effective preparation for delivery to cells and/or for administration to an individual. Suitable pharmaceutical carriers for use with the compositions are described in, for example, Remington's Pharmaceutical Sciences (18th Edition, A. R. Gennaro et al. Eds., Mack Publishing Co., Easton, Pa., 1990).

In one embodiment, the polynucleotides of the invention can be formulated for delivery to an individual as a nanoparticle preparation. Suitable nanoparticles are known in the art and are commercially available. For example, see Anderson et al., PNAS (2004) Vol. 101, pp 16028-16033.

In one embodiment, the polynucleotides of the invention are formulated in a composition for delivery to an individual by complexing the polynucleotides with a nanoparticle composition that is commercially available from Polyplus (Ilkrich, France). For example, the in vivo-jetPEI formulation available from Polyplus can be used to prepare compositions of the invention using conventional techniques and according to manufacture's instructions. Thus, in one embodiment, a composition of the invention comprises polynucleotides as described herein in physical association with nanoparticles.

There is no particular limitation to the route that the DNA polynucleotides of the invention can be delivered, with suitable routes including but not necessarily limited to enteral and parenteral routes. These routes of delivery include but are not limited to intramusclar injection, intraperitoneal injection, intravenous injection, intracranial, and oral delivery. The compositions may be injected directly into a solid tumor.

It will be recognized by those of skill in the art that the form and character of the particular dosing regime used for delivering the compositions of the invention will be dictated by the route of administration and other well-known variables, the sex and size of the individual, and the type and stage of the particular cancer being treated. Based on such criteria, one skilled in the art can determine an effective amount of a composition for use in the invention.

Compositions of the invention can be administered prior to, concurrently, or subsequent to conventional cancer therapies including but not limited to chemotherapies, surgical interventions, and radiation therapy.

The following Examples are intended to illustrate but not limit the invention.

Example 1

The materials and methods used in the invention include the following.

Cell culture—All cell lines were grown in monolayer on treated polystyrene cell culture dishes (Corning) at 37° C. in 3% $O_2$, 5% $CO_2$, and 97% relative humidity in HERA Cell 240 incubators. Human normal fibroblasts HCA2, IMR-90, and WI-38 used in this study were immortalized by constitutive expression of hTERT from integrated pBABE-Puro retrovirus. Immortalized human foreskin fibroblast line HCA2 and immortalized embryonic lung fibroblast IMR-90 and WI-38 were maintained in MEM (ATCC) supplemented with 15% fetal bovine serum; FBS, (Gibco) and 1× Pen/Strep (Gibco). Normal human mammary epithelial cells HMEC1, HMEC2 and HMEC4 (Clonetics) were maintained in MEBM (Lonza) and supplemented with MEGM SingleQuots (Lonza) which contains BPE, hEGF, insulin, hydrocortisone, and GA-1000. Human fibrosarcoma cell line HT1080 (ATCC), human embryonic kidney line GP2-293 (Clontech) and human cervical carcinoma line HeLa (ATCC) were maintained in DMEM (Gibco) supplemented with 10% FBS (Gibco), 1× Pen/Strep (Gibco) and 1× Non-essential amino acids (Gibco). Breast epithelial carcinoma line MDA-MB-468 (ATCC) was maintained in Leibovitz L-15 (ATCC) supplemented with 10% FBS and 1× Pen/Strep. Breast epithelial carcinoma line HCC-1954 (ATCC) was maintained in RPMI-1640 (ATCC) and supplemented with 10% FBS and 1× Pen/Strep. Breast epithelial carcinoma T47-D (ATCC) was maintained in RPMI-1640 supplemented with 10% FBS, 1× Pen/Strep and 0.01 mg/ml bovine insulin (Sigma I 4011). Breast epithelial carcinoma line MCF7 (ATCC) was maintained in MEM and supplemented with 10% FBS, 1× Pen/Strep and 0.01 mg/ml bovine insulin.

Cloning of the human Rad51 promoter region and construction of pRad51-GFP, pRad51-Luc, and pRad51-DTA plasmids—The 6,532 by Rad51 regulatory region (the sequence provided as SEQ ID NO:1) was cloned in two steps. In the first step, the region from 2,930 by upstream to 230 by downstream from the start of transcription was PCR amplified using the GC Rich PCR Kit (Roche) with the primers 5'-AACATTAATGCACAGCAGGTGAG-CAGCTAGCAAGCAAGC-3' (SEQ ID NO:6) and 5'-CG-CACCGGTGCCATTACTCGGTCCG-CAGCGCTCCTCTCTCCAGC-3', (SEQ ID NO:7) and subcloned into the pEGFP-N1 plasmid (Clontech) to replace the original CMV promoter by digesting both the PCR product and plasmid with the restriction enzymes AseI+AgeI resulting in pRad51(½) plasmid. In the second step, primers 5'-TCTGTAAACTCGCGCAGGATCAAGCTCTCG-3' (SEQ ID NO:8) and 5'-TCCACCGGTGTATCTG-CATTTGCTTCAAGCTGCATCTGC-3' (SEQ ID NO:9) were used to PCR amplify 164 by upstream to 3,602 by downstream from the Rad51 transcription start site. An internal EcoRI site located 23 by upstream of the start of transcription and the oligo-introduced AgeI sites were used to digest both the PCR product and pRad51(½) plasmid, followed by ligating the Rad51 gene fragment from 2,930 bp upstream to 24 by upstream to the start of transcription with the fragment containing 23 by upstream to 3,602 by downstream of the start of transcription. This two-step method reconstitutes the wild type full length 6,532 by Rad51 regulatory region; containing 2,930 bp upstream to 3,602 by downstream from the start of transcription (SEQ ID NO:1. The regulatory region includes the start of transcription, the first exon (non-coding), the first intron, and the first 40 by of the second exon (coding), with the GFP gene ligated in frame after the 40 by second exon fragment. Final pRad51-GFP plasmid was tested by restriction enzyme digestion and sequencing.

To transfer the full 6,532 bp Rad51 promoter region to the promoterless pGL3-Basic (Promega), which contains the gene for firefly luciferase, the restriction enzyme sites AgeI and AseI had to be introduced into pGL3-Basic polylinker by site-directed mutagenesis (Stratagene) with the following primers: 5'-CCGGAAGCTTACCGGTCGCCACCATG-GAAGACGCC-3' (SEQ ID NO:10) and 5'-GCCAAGCT-TAATTAATTCGCAGATCTCGAGCC-3' (SEQ ID NO:11) resulting in pGL3-Basic(Age/Ase) vector. The full length Rad51 promoter region was then cut out of the pRad51-GFP plasmid by the restriction enzymes AseI and AgeI and cloned into the same sites in pGL3-Basic to create pRad51-Luc, with the translational start of the firefly luciferase gene in frame with the first twelve amino acids of the Rad51 coding region and under the Rad51 promoter.

To construct pRad51-DTA, which contains the Rad51 promoter controlling bacterial diphtheria toxin A (DTA) gene, GFP was excised from pRad51-GFP with the restriction enzymes AgeI and NotI and replaced with the gene encoding DTA. The DTA gene was obtained by PCR amplifying the DTA coding sequence from plasmid pROSA26KPN with the following primers to introduce an AgeI site at the 5' end and a NotI site at the 3' end: 5'TTAGCGGCCGCTTAGAGCTT-TAAATCTCTGTAGGTAG-3' (SEQ ID NO:12) and 5'-CCTACCGGTCGCCACCATGGATCCTGAT-GATGTTG-3'(SEQ ID NO:13).

Western Blots—Exponentially growing cells were harvested and counted on a Beckman Coulter Z2 Particle Counter. Cells were resuspended in PBS pH 7.4 (Gibco) with Complete Protease Inhibitor Cocktail (Roche) and lysed by mixing with Laemmli sample buffer (BioRad) containing 5% 2-Mercaptoethanol (J. T. Baker), followed by boiling for 10 minutes with vortexing every 5 minutes. Protein concentration was determined by DC protein assay (BioRad). Protein extracts (25 µg) from each cell line were separated on a 10% SDS-PAGE, blotted onto a nitrocellulose membrane (Bio-Rad) and blocked in TBS-T with 1.25% dried milk (w/v). Membranes were probed with mouse monoclonal primary antibodies against human Rad51 (NeoMarkers) overnight or α-tubulin (Abcam) for two hours and probed with HRP conjugated goat anti-mouse secondary antibodies (BioRad) for two hours. The images were analyzed using ImageQuantTL (Amersham).

Quantitative RT-PCR—Exponentially growing cells where harvested and counted on a Beckman Coulter Z2 Particle Counter. mRNA was extracted using the RNeasy Mini Kit and QIAshredder (Qiagen) and concentrations were determined by A260 nM spectrophotometry on a SmartSpec Plus (BioRad). Titan One-Tube RT-PCR (Roche) kit was used to amplify the 5' of Rad51 mRNA using 0.4 µg of total mRNA and primers 5'CCAGAGACCGAGCCCTAAGGAGAGT-GCG-3' (SEQ ID NO:14) and 5'-TGGCATTTATGCCA-CACTGCTCTAACCGTG-3'. (SEQ ID NO:15) The following PCR program was used to quantify the main transcript: 1) heat 0.4 µg of RNA sample in 16 µL ddH$_2$O at 85° C. for 3 min; 2) add enzyme/primer/dNTP mix; 3) 50° C. for 30 min; 4) 94° C. 2 for minutes; 5) 10 cycles of 94° C. for 1 min, 60° C. for 1 min, 68° C. for 1 minute; 6) 15 cycles of 94° C. for 1 minute, 60° C. for 1 min, 68° C. for 1 min+5 sec/cycle; 7) 68° C. for 7 minutes. A similar PCR program was run to examine the smaller alternative splice variant at the 5' end, with an additional 5 cycles at the step 6. Control PCR reaction was performed at the same conditions as experimental reaction with primers for 18S ribosomal subunit from QuantumRNA 18S Internal Standards Kit (Ambion) at 3:7 18S primer:competimer mix. PCR products were run on a 1.5% agarose gel and analyzed by ImagequantTL (Amersham).

Rad51 promoter activity and luciferase assays—Two µg of pRad51-Luc or 2 µg of the pEGFP-N1 (Clontech) were transfected into $1 \times 10^6$ growing cells of each of the thirteen cell lines by Amaxa Nucleofector II electroporation. The following programs Nucleofector programs and transfection solutions were used for each cell line: HCA2, program U-20 and solution NHDF; IMR-90, program X-001 and solution NHDF; WI-38, program V-001 and solution NHDF; HMEC1, HMEC2, and HMEC4, program Y-001 and solution HMEC; MDA-MB-468, program X-005 and solution V; HT1080, program L-005 and solution V; GP2-293, program A-023 and solution V; HCC 1954, program A-023 and solution V; T47-D, program A-023 and solution V; MCF7, program P-020 and solution V; and HeLa, program 1-013 and solution V. Cells transfected with pEGFP-N1 were harvested 72 hours post transfection and analyzed by FACS analysis to determine the percentage of cells with detectable GFP. Cells transfected with pRad51-Luc were harvested and counted 72 hours post transfection and lysed using passive lysis buffer (Promega) at a ratio of 200 µl/$1 \times 10^6$ cells and then 20 µl of this extract was used in the luciferase assay (Promega) using a GloMax20/20 Luminometer (Promega).

Analysis of the effect of Rad51 promoter driven DTA on the cells: cell counts and luciferase assay—Cells were split, and 24 hours later $1 \times 10^5$ cells of each cell line were co-transfected with 0, 0.01, 0.02, 0.04, 0.08 or 0.1 µg of pRad51-DTA supplemented with the control pGL3 basic plasmid to bring the amount of DNA to 0.1 µg in each transfection, along with 1 µg of pGL3-Control plasmid containing firefly lucifrerase under the SV40 promoter using a Fugene 6 Transfection Reagent (Roche). Cells were harvested 72 hours post transfection and counted by Z2 Particle Counter (Beckhman Coulter), and protein extracts were obtained by lysing cells with passive lysis buffer (Promega) at a ratio of 50 µl/50,000 cells. Twenty µl of the extract were used for each luciferase assay.

To measure cell survival after pRad51-DTA transfection (FIG. 3B) it is essential to calculate the survival of transfected cells, since the total cell count obtained 3 days after transfection with pRad51-DTA includes nontransfected cells that continue to proliferate, while cells that are killed by DTA do not proliferate. To calculate the percent survival of transfected cells ($S_T$) we used the formula:

$$S_T = T_{SE}/T_{SC} \times 100\%$$

where $T_{SE}$ is the number of transfected cells (cells that received the plasmid) that survived after transfection with pRad51-DTA, and $T_{SC}$ is the number of transfected cells that survived after control transfection with the GFP vector. $T_{SE}$ and $T_{SC}$ are calculated as $$T_{SE \text{ or } SC} = H - kN$$

where H is the total number of cells harvested 3 days after transfection, k is the growth rate of nontransfected cells, calculated as the number of cells harvested 3 days after the control (GFP) transfection divided by the number of cells plated. N is the number of cells that did not receive the plasmid, calculated as the total number of cells used for transfection multiplied by transfection efficiency.

The experiment measuring the decline in luciferase activity after pRad51-DTA transfection relative to the control transfection (FIG. 3C) did not require a correction for transfection efficiency. This is because only the transfected cells were expressing luciferase.

Example 2

This Example demonstrates that Rad51 protein and mRNA are elevated in cancer cells. In particular, we examined the endogenous levels of Rad51 protein and transcripts in a panel of human cancer and normal cell lines including: four breast cancer cell lines HCC-1954, MDA-MB-468, T47-D, and MCF7; cervical cancer cell line HeLa; fibrosarcoma line HT1080; transformed kidney cells GP2-293; three lines of normal fibroblasts HCA2, IMR-90, WI-38; and three normal human mammary epithelial cell lines HMEC1, HMEC2, and HMEC4.

Rad51 transcript was examined using quantitative RT-PCR (FIG. 1A, B) with primers to exons 1-3. The levels of Rad51 transcript were greater in cancer cells than in the normal cells (P=0.001, t-test). On average (by pooling the data for all of the non-cancerous cells versus the cancerous cells) cancer cells had 3.5-fold increase in the transcript levels. The cell line with the strongest Rad51 expression was T47-D, which had over a 12.2-fold increase when compared to HMEC4; which had the least amount.

An alternatively spliced form of Rad51 is believed to have higher translation efficiency than the main transcript (Hasselbach L, et al. (2005) Eur J Gynaecol Oncol 26: 589-98). This form is also associated with an increased cancer risk in BRCA2 carriers (Antoniou A C, et al. (2007) Am J Hum Genet 81: 1186-200). Therefore, we also compared the levels of the alternatively spliced transcript in normal and cancer cells using quantitative RT-PCR (FIG. 1C). The cell lines HCA2, WI-38, and GP2-293 did not have detectable alternative transcripts; while HCC1954, T47-D, and MCF-7 had the highest levels (FIG. 1C). On average, cancer cells showed a 2.5-fold increase in the alternatively spliced Rad51 transcript, and this difference was statistically significant (P=0.037, t-test).

We next analyzed the Rad51 protein levels in the 13 cell lines by Western Blot (FIG. 1D). The analysis shows that Rad51 is more abundant in cancer cells when compared to normal cells (P=0.001, t-test). Rad51 protein levels were the greatest in T47-D cells and the lowest in HCA2, resulting in a 25-fold differential.

Example 3

This Example demonstrates that Rad51 promoter activity is dramatically increased in cancer cells. To test whether the differential expression of Rad51 can be utilized for anticancer therapy we cloned the putative Rad51 regulatory region including 2,930 nucleotides upstream to 3,602 nucleotides downstream from the start of transcription (37, 39) (FIG. 1A) from total DNA isolated from normal human cells. We then cloned the GFP ORF under the control of the Rad51 promoter. The resulting construct, pRad51-GFP, contains the 2,930 bp of upstream regulatory sequences, the first noncoding exon of the Rad51, and the first 12 amino acids of the Rad51 ORF. pRad51-GFP, was transfected into HCA2, HT1080, and GP2-293 cells, and GFP expression was analyzed by flow cytometry. The two cancer cell lines, HT1080 and GP2-293 showed a large number of GFP+cells (67% in GP2-293 and 34% in HT1080). Surprisingly, no GFP+ cells were detectable in the normal human fibroblasts HCA2. This result suggested that the difference in Rad51-GFP expression between the two cancer cell lines and the normal cells was much more dramatic than the difference in endogenous Rad51 levels.

Figure 2:
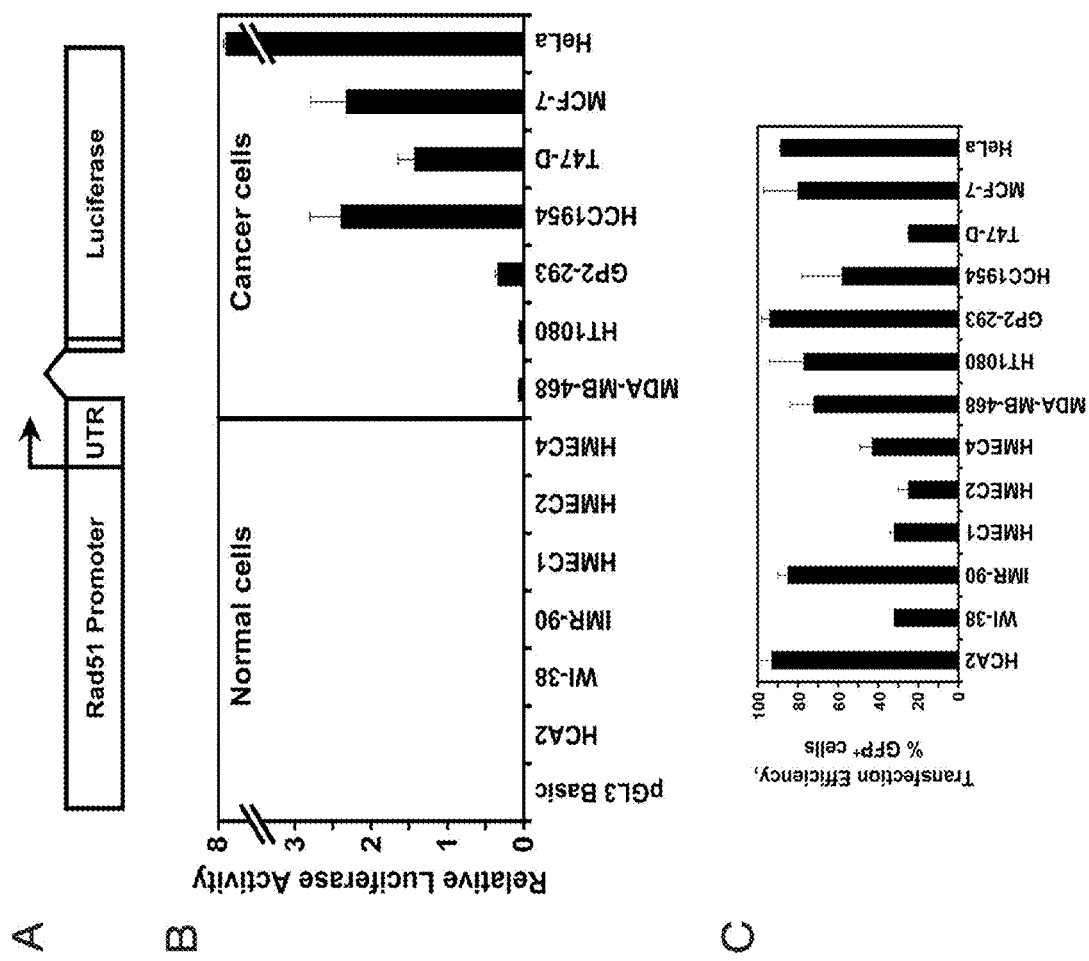
FIGS. 2A-2C illustrate that a Rad51 promoter driven transcription of a transgene shows dramatic difference in promoter activity between normal and cancer cells. (A) Diagram of the pRad51-Luc construct with the firefly luciferase gene under control of Rad51 promoter. Transcription start site is indicated by arrow. (B) Luciferase assays measuring Rad51 promoter activity in 13 cell lines. Cells were transfected with 2 μg of pRad51-Luc and luciferase activity was analyzed in cell extracts 72 hours posttransfection. Luciferase activity was normalized for the efficiency of transfection determined by transfection with GFP-expressing plasmid, shown in C. The values for luciferase activity for all the cell lines are provided in Table 1. The experiments were repeated three times and error bars show s.d. (C) Transfection efficiency in 13 cell lines. In parallel with pRad51 luciferase transfections shown in B, cells were transfected with 2 μg of the GFP-expressing plasmid pEGFP-N1 and analyzed by flow cytometry 72 hours posttransfection. The parameters for FACS analysis were set so as to detect all cells with green fluorescence above the background. This ensures that all transfected cells are scored regardless of the differences in expression in different cell lines. Efficiency of transfection is expressed as the percentage of GFP+ cells. The experiments were repeated three times and error bars show s.d.

Since the expression of Rad51-GFP was virtually undetectable in normal cells, we replaced GFP with firefly luciferase (FIG. 2A), a more sensitive reporter. The resulting construct, pRad51-Luc, was transfected into the panel of 13 cancer and normal cells lines and 72 hours post transfection cell extracts were tested for luciferase activity (FIG. 2B). To normalize for differences in transfection efficiency, cells were transfected with pEGFP-N1 vector and the number of cells with detectable GFP fluorescence was scored by flow cytometry (FIG. 2C). The ratio between luciferase activity and the number of GFP+cells was used as a measure of Rad51-Luc expression. All the cancer cell lines displayed dramatically elevated Rad51 promoter activity (FIG. 2B and Table 1).

There was up to a 12,500-fold difference in luciferase activity between the lowest activity cell line (HCA2) and the highest (HeLa). On average, cancer cells displayed over a 840-fold higher Rad51 promoter activity than the normal cells. This difference in promoter activity is striking, and is much greater than the difference observed in the endogenous protein and transcript levels. Thus, compositions comprising the Rad51 promoter in which Rad51 ORF is replaced with a reporter or a cytotoxic gene represent unprecedented properties useful for transcriptional gene therapy.

TABLE 1

| Cell line | Relative Light Units | SD |
| --- | --- | --- |
| pGL3 Basic (negative control) | 488 | 103 |
| HCA2 | 639 | 326 |
| WI-38 | 963 | 408 |
| IMR-90 | 1,333 | 720 |
| HMEC1 | 4,450 | 1,157 |
| HMEC2 | 5,476 | 548 |
| HMEC4 | 2,054 | 308 |
| MDA-MB-468 | 63,140 | 6,945 |
| HT1080 | 53,394 | 4,806 |
| GP2-293 | 341,995 | 27,360 |
| HCC1954 | 2,394,231 | 407,019 |
| T47-D | 1,427,920 | 214,188 |
| MCF-7 | 2,322,569 | 464,514 |
| HeLa | 7,998,790 | 39,988 |

Example 4

Figure 3:
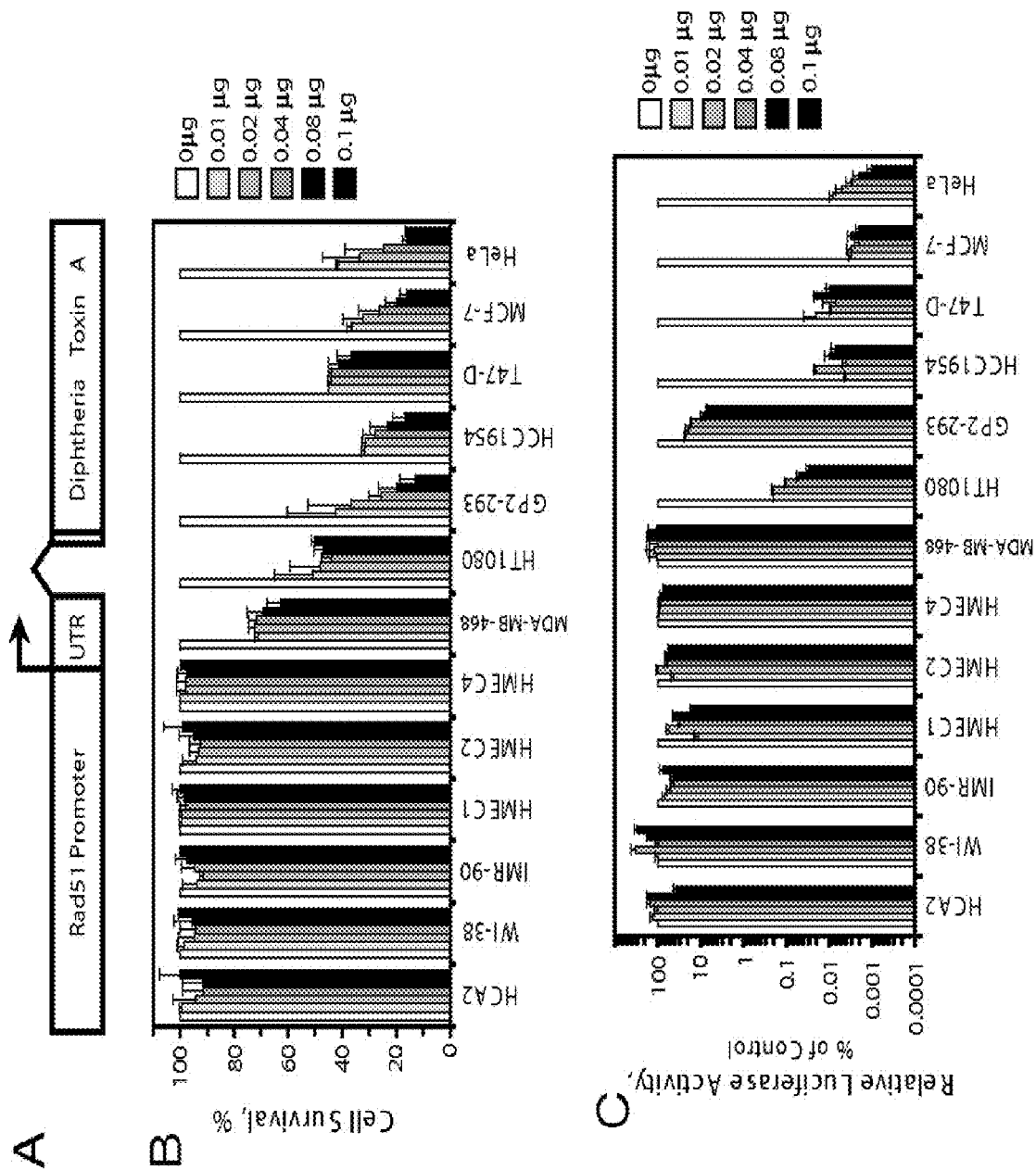
FIGS. 3A-3C illustrate that a construct comprising a Rad51 promoter fused to diphtheria toxin A (DTA) gene selectively kills cancer cells. (A) Diagram of the pRad51-DTA construct. Transcription start site is indicated by arrow. (B) Decline in cell counts after transfection with pRad51-DTA. Cells were co-transfected with the indicated amounts of pRad51-DTA and promoterless plasmid pGL3 to bring the total amount of DNA in each transfection to 0.1 µg. Attached cells were harvested 72 h posttransfection and counted using a Beckman Coulter counter. For each cell line, the cell counts obtained after transfection with pRad51-DTA were divided by cell counts in the control transfections with 0 µg of pRad51-DTA, and normalized for the efficiency of transfection. The experiments were repeated three times and error bars show s.d. (C) Inhibition of protein synthesis by pRad51-DTA. In this experiment inhibition of SV40-luciferase expression is used as a model of reduction in de novo protein synthesis by DTA. Cells were transfected with pRad51-DTA and pGL3 as described above along with 1 µg of a plasmid encoding firefly luciferase under SV40 promoter. Cells were harvested 72 h posttransfection and subjected to luciferase assay. For each cell line, luciferase activity after transfection with pRad51-DTA was divided by luciferase activity in control transfections with 0 µg of pRad51-DTA. The experiments were repeated three times and error bars show s.d.

This Example demonstrates that a Rad51 promoter operatively linked to a cytoxic agent can be used to selectively kill cancer cells with minimal effect on normal cells. To test whether the Rad51 promoter fused to a cytotoxic gene will selectively kill cancer cells, we cloned the diphtheria toxin A (DTA) ORF under the control of the Rad51 promoter (FIG. 3A). We then examined the effect of the Rad51-DTA fusion on cancer and normal cells. We used two approaches to measure the toxicity to the cells: decline in cell counts, and inhibition of protein synthesis. The panel of 13 cell lines was transfected with increasing amounts of pRad51-DTA plasmid and/or the promoterless pGL3 plasmid. Complementing amounts of pGL3 were added so as to keep the amount of plasmid DNA equal in each transfection. Cells were allowed to express the transgene for 72 hours, attached cells were harvested, and then counted using a Beckman Coulter cell counter. Transfection efficiency was determined by transfecting the cells with a GFP vector in the absence of DTA. DTA inhibits protein synthesis and triggers apoptosis and detachment of cells, although the attached fraction may contain some cells at early stages of apoptosis. The killing effect (FIG. 3B) at each dose of the pRad51-DTA was expressed as a percent of attached cells transfected with Rad51-DTA construct relative to the transfection with the control plasmid pGL3 (see Example 1). pRad51-DTA did not cause a decline in cell counts in any of the normal cell lines. However, all cancer cells lines displayed 30-80% reduction in cell survival. The observed killing effect is likely to be an underestimate, as some early apoptotic cells are counted as attached cells.

To measure inhibition of protein synthesis, we co-transfected a pRad51-DTA and control plasmid, as described above, with the firefly luciferase gene under the control of the SV40 promoter/enhancer element. Cells were harvested 72 hours post transfection and luciferase activity was measured in the protein extracts (FIG. 3C). Reduction in luciferase activity was used as a measure of the inhibition of protein synthesis. Protein synthesis in the six normal cell lines either did not change or decreased at most 10-fold. One of the cancer cell lines, MDA-MB-468, did not show a change, but the other six cancer cell lines had reductions in protein synthesis that ranged from 10 up to 100,000 fold. Various amounts of transfected pRad51-DTA had similar toxicities, which is consistent with the fact that very low levels of DTA are sufficient to kill the cell. In summary, the Rad51-DTA construct displayed moderate to very strong toxicity to six out of seven cancer cell lines that were tested, and had minimal toxicity to normal cells.

Example 5

This Example demonstrates use of the Rad51 promoter for transcriptionally targeted anti-cancer therapy in an animal model.

Mouse xenografts were created using 5,000,000 HeLa (human cervical cancer) cells, suspended in 200 µL of 20% Matrigel in PBS injected subcutaneously into the lower back of Athymic nude mice. This procedure established tumors in 100% of mice on which it was performed (n=6). After approximately two weeks, the tumors reach a size of about 100 mm$^2$ and are suitable for treatment according to the method of the invention.

While it is expected that a variety of pharmaceutical preparations can be used for delivery of the polynucleotides of the invention for in vivo cancer therapy, for this Example, a commercially available nanoparticle delivery system (Polyplus (in vivo jetPEI)) was used. Briefly, we used a complex of 20-50 µg of either Rad51 promoter-DTA (SEQ ID NO:1 used for the Rad51 promoter and SEQ ID NO:4 for the DTA) or Rad51 promoter-luciferase (or GFP) with in vivo jetPEI nano particles per manufacturer's instructions (6.25 µg DNA/1 µg jetPEI) in a 100 µL volume of 5% glucose solution in water.

The volume of each tumor was measured, and the composition comprising the Rad51 promoters operably linked to diphtheria toxin or reporter gene was injected directly into the tumor. After 10 days the mouse was sacrificed, the tumor volume measured, the tumor excised and weighed. The results are as follows: One mouse was treated with Rad51-DTA complexed with jetPEI and one mouse was treated with Rad51-luciferase complexed with jetPEI. Both tumors grew when tumor volume was measured outside in the live mouse, but when tumors were excised, the mass to volume ratio for the Rad51-DTA treated mouse was 0.21 mg/mm$^3$ versus 0.82 mg/mm$^3$ for the mouse treated with Rad51-luciferase. Thus, the tumor in the mouse that received the Rad51 promoter-DTA had a 44% decrease in volume. The tumor in the mouse that received the Rad51 promoter-luciferase had a 130% increase in tumor volume. Moreover, the tumor in the mouse that received the Rad51 promoter-DTA exhibited no detectable angiogenesis, while the tumor in the mouse that received the Rad51 promoter-luciferase exhibited detectable angiogenesis. (Angiogenesis was detected by dissecting the tumor from the mouse post-mortem and visually observing, using both the naked eye and inverted light microscope for the presence of blood vessels.) Therefore, the present invention is demonstrated to be suitable for inhibiting growth of cancer cells in an individual, as evidenced by inhibiting an increase of mass of an in vivo tumor. Further, the compositions and methods of the invention can inhibit angiogenesis in tumors.

As will be appreciated from the foregoing Examples and description of the invention, the Rad51 gene promoter is an effective cancer-specific promoter for transcriptionally targeted therapy. Therapies based on the expression of suicide genes driven by cancer-specific promoters has been attempted with several promoters, most notably with the hTERT (human telomerase) promoter. However, our results indicate that the Rad51 promoter offers unexpected superior strength and selectivity. In particular, the activity of hTERT promoter was shown to be on average 10-fold higher in cancer cells than in the normal cells (Komata T, et al. (2001) Cancer Res 61: 5796-802; Gu J, et al. (2000) Cancer Res 60: 5359-64; 'Abdul-Ghani R, et al. (2000) Mol Ther 2: 539-44; Takakura M, et al. (1999) Cancer Res 59: 551-7), while with Rad51 promoters described herein we observe up to 12,500-fold increase in promoter activity. In a study that used an hTERT-DTA fusion for selective killing of cancer cells (Abdul-Ghani R, et al. (2000) Mol Ther 2: 539-44), hTERT-DTA decreased protein synthesis up to 68%, while with Rad51-DTA we observed up to 100,000-fold decrease in protein synthesis using similar amount of DTA-expressing construct. Furthermore, overexpression of Rad51 in tumors has been described before (6-8), however, no attempts have been made to exploit it for transcriptionally targeted therapy, likely because the difference in endogenous protein expression between normal and cancer cells would not be expected to provide a meaningful therapeutic benefit. Serendipitously, we found that when the Rad51 promoter is fused to another ORF an unprecedented difference in promoter activity between normal and cancer cells is achieved.

While the invention has been described through illustrative examples, routine modifications will be apparent to those skilled in the art, which modifications are intended to be within the scope of the invention.

We claim:

1. A composition comprising a polynucleotide, wherein the polynucleotide comprises a Rad51 promoter comprising the sequence of SEQ ID NO:1, wherein the Rad51 promoter is operably linked to a coding region for a cytotoxic agent.

2. The composition of claim 1, wherein the cytotoxic agent is bacterial diphtheria toxin A.

3. The composition of claim 1, wherein the composition further comprises nanoparticles in physical association with the polynucleotide.

4. A method for inhibiting growth of cancer cells comprising delivering to the cells an effective amount of a composition comprising a polynucleotide, wherein the polynucleotide comprises a Rad51 promoter, wherein the Rad51 promoter comprises the sequence of SEQ ID NO:1, wherein the Rad51 promoter is operably linked to a coding region for a cytotoxic agent, and wherein subsequent to delivering the composition to the cells the growth of the cells is inhibited.

* * * * *